(12) United States Patent
Nakae et al.

(10) Patent No.: US 6,580,280 B2
(45) Date of Patent: Jun. 17, 2003

(54) MULTILAYERED GAS SENSOR AND A RELATED GAS CONCENTRATION DETECTING SYSTEM

(75) Inventors: Makato Nakae, Toyoake (JP); Syuichi Nakano, Kariya (JP); Toshitaka Saito, Toyohashi (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/002,132

(22) Filed: Dec. 5, 2001

(65) Prior Publication Data

US 2002/0070736 A1 Jun. 13, 2002

(30) Foreign Application Priority Data

Dec. 8, 2000 (JP) ......................... 2000-374767

(51) Int. Cl.[7] .................. G01R 27/08; G01R 23/20; G01N 27/62; G01N 27/00
(52) U.S. Cl. .................. 324/717; 324/468; 324/464; 324/722; 324/71.5
(58) Field of Search .................. 324/717, 468, 324/464, 722, 71.5; 204/429, 426, 424; 73/23.31, 35.07, 35.08, 23.2

(56) References Cited

U.S. PATENT DOCUMENTS

| | | | | |
|---|---|---|---|---|
| 4,130,797 A | * | 12/1978 | Hattori et al. | 324/722 |
| 4,419,190 A | * | 12/1983 | Dietz et al. | 205/785 |
| 4,505,802 A | * | 3/1985 | Mase et al. | 204/425 |
| 4,721,084 A | * | 1/1988 | Kawanabe et al. | 123/440 |
| 4,775,838 A | * | 10/1988 | Mizuta et al. | 324/468 |
| 4,915,815 A | * | 4/1990 | Shibata et al. | 204/429 |
| 5,405,521 A | * | 4/1995 | Nakamori et al. | 204/425 |
| 5,781,878 A | * | 7/1998 | Mizoguchi et al. | 701/109 |
| 5,889,196 A | * | 3/1999 | Ueno et al. | 73/23.31 |
| 5,935,400 A | * | 8/1999 | Takami et al. | 204/425 |
| 5,948,963 A | * | 9/1999 | Kato et al. | 73/23.2 |
| 6,084,418 A | | 7/2000 | Takami et al. | 324/717 |
| 6,096,187 A | * | 8/2000 | Mizoguchi et al. | 205/784.5 |
| 6,222,372 B1 | * | 4/2001 | Fukaya et al. | 324/464 |
| 6,453,724 B1 | * | 9/2002 | Kawase et al. | 73/23.31 |

FOREIGN PATENT DOCUMENTS

JP          9-292364          11/1997

* cited by examiner

Primary Examiner—Christine Oda
Assistant Examiner—Wasseem H. Hamdan
(74) Attorney, Agent, or Firm—Nixon & Vanderhye P.C.

(57) ABSTRACT

An exhaust gas side electrode is provided on one surface of a solid electrolytic substrate. A reference gas side electrode is provided on an opposite surface of the solid electrolytic substrate so as to be exposed to a reference gas stored in a reference gas chamber. Each lead of the electrode is connected to a signal output terminal. This sensor satisfies a relationship B/A<0.5, wherein 'A' represents an overall resistance value of an electric path including the solid electrolytic substrate, the electrodes, and their leads in a sensor activated condition, while 'B' represents a resistance value of the leads at a room temperature. Some embodiments may be arranged such that at least one of the leads has a low resistance portion located in the vicinity of the electrodes and a high resistance portion located in the vicinity of signal output terminals. For example, at least one lead may have a smaller resistance per unit length near the electrodes as compared to the resistance per unit length at a location far from the electrodes.

17 Claims, 11 Drawing Sheets

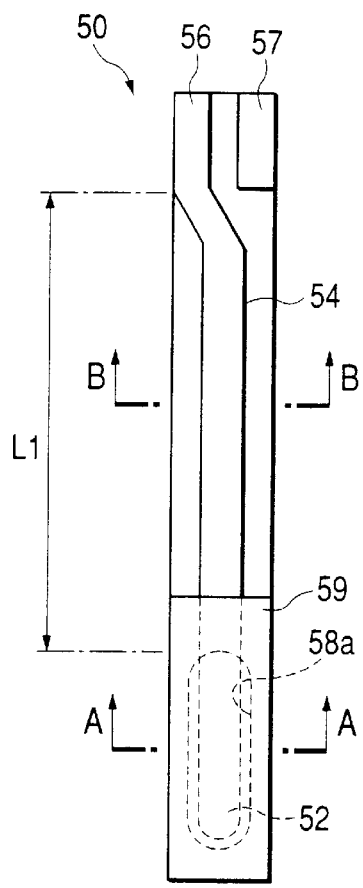
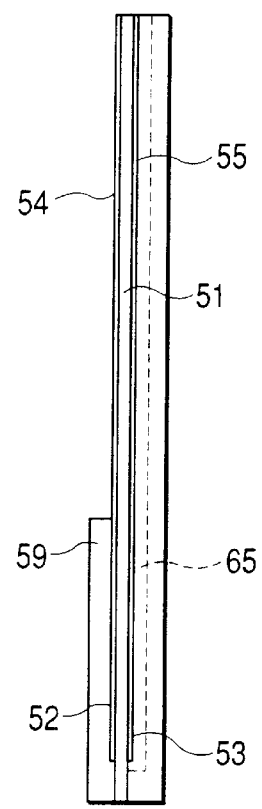
FIG. 3A
FIG. 3B
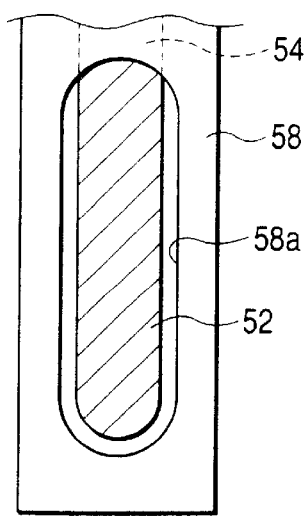
FIG. 4

MULTILAYERED GAS SENSOR AND A RELATED GAS CONCENTRATION DETECTING SYSTEM

BACKGROUND OF THE INVENTION

The present invention relates to a multilayered gas sensor and a gas concentration detecting system using this sensor.

The multilayered gas sensor has a sensing element which is maintained at an appropriate activated condition by controlling an element temperature (i.e., the temperature of a sensing element) to a predetermined temperature region.

To this end, the element temperature is periodically monitored and the electric power supplied to a heater is controlled to maintain the element temperature to a target value.

In general, the element temperature is indirectly monitored based on an element impedance (i.e., element resistance) known from a relationship between a voltage applied to the sensing element and an obtained sensor current.

FIG. 10 shows the temperature characteristics of a sensing element, according to which the element impedance increases with decreasing element temperature.

In general, the element impedance includes a resistance component of a solid electrolytic substrate and a resistance component of an electric lead portion. The solid electrolytic substrate has negative temperature characteristics according to which the resistance of the solid electrolytic substrate decreases with increasing temperature as indicated by a line ① shown in FIG. 17. On the contrary, the lead portion has positive temperature characteristics according to which the resistance of the lead portion increases with increasing temperature as indicated by a line ② shown in FIG. 17. In FIG. 17, a line ③ represents the change of element impedance (ZAC).

The element impedance is inherently a resistance component of the solid electrolytic substrate. However, the actually detected element impedance of a sensor includes a resistance component of the lead portion whose temperature characteristics is opposite to that of the solid electrolytic substrate. Especially, when the gas sensor is in an activated condition (i.e., in a higher temperature region), the percentage of the lead resistance becomes large. This leads to deterioration in the sensitivity of element impedance.

SUMMARY OF THE INVENTION

In view of the above-described problems, the present invention has an object to provide a multilayered gas sensor capable of accurately detecting an element impedance in the entire operating region of this sensor. Furthermore, the present invention provides a gas concentration detecting system capable of improving the temperature controllability by the use of the multilayered gas sensor of the present invention.

In order to accomplish the above and other related objects, the present invention provides a first multilayered gas sensor comprising a solid electrolytic substrate having oxygen ion conductivity, a measured gas side electrode provided on one surface of the solid electrolytic substrate, a reference gas side electrode provided on an opposite surface of the solid electrolytic substrate so as to be exposed to a reference gas stored in a reference gas chamber, a first lead having one end connected to the measured gas side electrode and the other end connected to a first signal output terminal, and a second lead having one end connected to the reference gas side electrode and the other end connected to a second signal output terminal. The first multilayered gas sensor is characterized in that the following relationship is satisfied $$B/A < 0.5$$

wherein 'A' represents an overall resistance value of an electric path including the solid electrolytic substrate, the electrodes, and the first and second leads in a sensor activated condition, while 'B' represents a resistance value of the first and second leads at a room temperature.

According to a preferred embodiment of the present invention, the overall resistance value 'A' is a target resistance value for a sensor activation control (i.e., an impedance control).

In short, a ratio of the lead resistance value 'B' to the overall resistance value 'A' is restricted to be less than 0.5. In other words, according to the first multilayered gas sensor, the percentage of the lead resistance with respect to the overall resistance can be restricted to a predetermined smaller value so as to adequately maintain or improve the sensitivity of element impedance. In other words, it becomes possible to enhance the correlation between the solid electrolytic resistance and the overall resistance. If required to assure more accuracy for the detection of element impedance, it will be preferable to restrict the ratio B/A to a more smaller value equivalent to 0.3 or less.

Practically, reducing the percentage of the lead resistance is feasible by reducing a resistance value of the lead portion. For example, it is preferable that at least one of the first and second leads has a lateral cross section equivalent to ½ to 5 times a lateral cross section of a corresponding electrode. It is also preferable that at least one of the first and second leads is thicker than the corresponding electrode. It is also preferable that at least one of the first and second leads is wider than the corresponding electrode.

Alternatively, reducing the percentage of the lead resistance is feasible by increasing a resistance value of the solid electrolytic substrate, although the time required to reach a sensor activated condition increases.

According to a preferable embodiment of the present invention, the first and second signal output terminals are provided at intermediate portions of the solid electrolytic substrate. This arrangement is advantageous to reduce the length of a lead connecting the sensor electrode (i.e., the measured gas side electrode or the reference gas side electrode) to its signal output terminal. As a result, the resistance value of the lead portion can be reduced.

Furthermore, it is preferable that the first and second leads contain a ceramic material to improve the adhesion properties and an additive amount of the ceramic material in at least one of the first and second leads is less than or equal to 12.5 wt %.

It is also preferable that at least one of the first and second leads is an electric conductive member having a resistance temperature coefficient less than or equal to $3 \times 10^{-3}/°$ C. If required to assure more excellent performance, it will be preferable that the electric conductive member has a resistance temperature coefficient less than or equal to $2.5 \times 10^{-3}/°$ C.

According to a preferable embodiment of the present invention, the electrodes are bonded on the surfaces of the solid electrolytic substrate and an insulating layer having a low thermal conductivity is provided to isolate the first and second leads from the solid electrolytic substrate.

In a sensor activated condition, the solid electrolytic substrate has a higher temperature. As understood from the characteristics shown in FIG. 17, the adverse influence of lead resistance increases when the temperature is high. In this respect, providing the insulating layer having a low thermal conductivity makes it possible to effectively prevent the temperature of the lead portions from increasing excessively. As a result, it becomes possible to improve the temperature characteristics of the sensor.

The gas sensor is generally equipped with a heater to increase the temperature of each electrode. However, the provision of a heater causes a temperature distribution in the gas sensing element in such a manner the temperature is high in the vicinity of the electrodes compared with the signal output terminals and their vicinities. Considering such temperature distribution, it is effective to reduce the resistance value of a limited lead portion closer to the electrodes.

In view of the above, the present invention provides a second multilayered gas sensor comprising a solid electrolytic substrate having oxygen ion conductivity, a measured gas side electrode provided on one surface of the solid electrolytic substrate, a reference gas side electrode provided on an opposite surface of the solid electrolytic substrate so as to be exposed to a reference gas stored in a reference gas chamber, a first lead having one end connected to the measured gas side electrode and the other end connected to a first signal output terminal, a second lead having one end connected to the reference gas side electrode and the other end connected to a second signal output terminal, and a heater for heating the electrodes. The second multilayered gas is characterized in that at least one of the first and second leads has a low resistance portion located in the vicinity of the electrodes and a high resistance portion located in the vicinity of the signal output terminals.

This arrangement makes it possible to selectively or effectively reduce the resistance value of a lead portion located closely to the electrodes. In other words, according to the second multilayered gas sensor, the percentage of the lead resistance with respect to the overall resistance can be restricted to a predetermined smaller value so as to adequately maintain the sensitivity of element impedance. As a result, it becomes possible to improve the temperature characteristics of the sensor. In other words, a detected element impedance explicitly reflects a resistance change of the solid electrolytic substrate.

According to a preferable embodiment of the present invention, a lateral cross section of the high resistance portion is smaller than that of the low resistance portion. This makes it possible to reduce the cost of the lead portions which are usually a platinum or other noble metallic member.

The present invention provides a third multilayered gas sensor comprising a solid electrolytic substrate having oxygen ion conductivity, a measured gas side electrode provided on one surface of the solid electrolytic substrate, a reference gas side electrode provided on an opposite surface of the solid electrolytic substrate so as to be exposed to a reference gas stored in a reference gas chamber, a first lead having one end connected to the measured gas side electrode and the other end connected to a first signal output terminal, a second lead having one end connected to the reference gas side electrode and the other end connected to a second signal output terminal, and a heater for heating the electrodes. The third multilayered gas sensor is characterized in that at least one of the first and second leads is configured in such a manner that a resistance value per unit length is smaller at a portion near the electrodes and is larger at a portion far from the signal output terminals.

This arrangement makes it possible to selectively or effectively reduce the resistance value of a lead portion located closely to the electrodes. In other words, according to the third multilayered gas sensor, the percentage of the lead resistance with respect to the overall resistance can be restricted to a predetermined smaller value so as to adequately maintain or improve the sensitivity of element impedance. As a result, it becomes possible to improve the temperature characteristics of the sensor. In other words, a detected element impedance explicitly reflects a resistance change of the solid electrolytic substrate.

According to the preferable embodiment of the present invention, the third multilayered gas sensor satisfies the following relationship $$B/A<0.5$$

wherein 'A' represents an overall resistance value of an electric path including the solid electrolytic substrate, the electrodes, and the first and second leads in a sensor activated condition, while 'B' represents a resistance value of the first and second leads at a room temperature.

In this case, the overall resistance value 'A' is a target resistance value for a sensor activation control (i.e., an impedance control).

Moreover, it is preferable that first to third multilayered gas sensor of the present invention further comprise a resistance detecting means for detecting a resistance value of the solid electrolytic substrate based on electric signals obtained from the signal output terminals, and a heater control means for controlling electric power supplied to a heater based on the resistance value detected by the resistance detecting means.

BRIEF DESCRIPTION OF THE DRAWINGS

The above and other objects, features and advantages of the present invention will become more apparent from the following detailed description which is to be read in conjunction with the accompanying drawings, in which:

FIG. 3A is a plan view showing a sensing element in accordance with the first embodiment of the present invention;

FIG. 3B is a side view showing the sensing element in accordance with the first embodiment of the present invention;

FIG. 4 is an enlarged plan view showing a detailed arrangement of the sensing element in accordance with the first embodiment of the present invention;

DESCRIPTION OF THE PREFERRED EMBODIMENT

Figure 1:
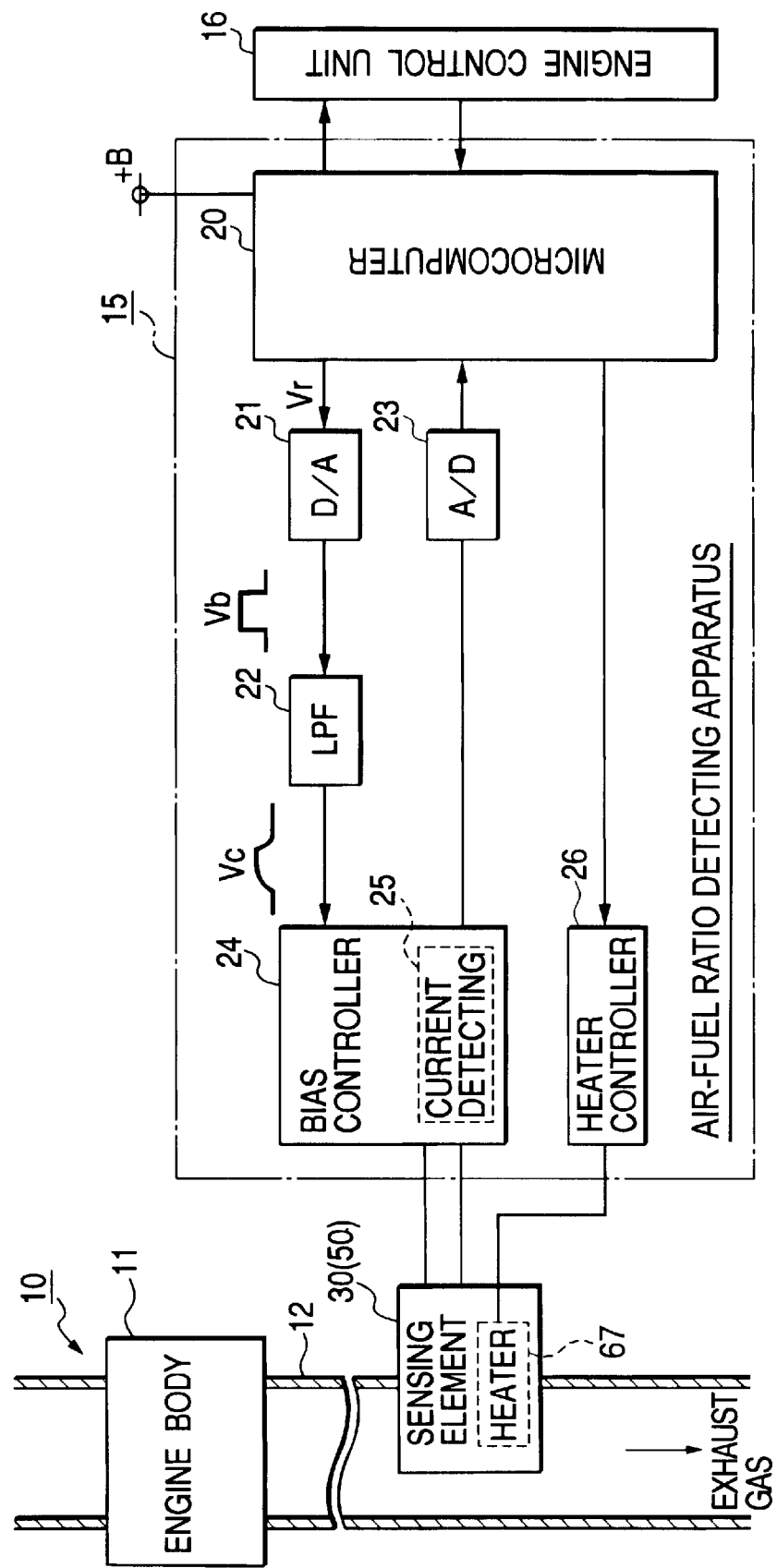
FIG. 1 is a circuit diagram showing a schematic arrangement of an air-fuel ratio detecting apparatus in accordance with a first embodiment of the present invention.

A preferred embodiment of the present invention will be explained hereinafter with reference to attached drawings. Identical parts are denoted by the same reference numerals throughout the drawings.

First Embodiment

The first embodiment of this invention relates to an air-fuel ratio sensing apparatus incorporated with a fuel injection control system for an internal combustion engine (gasoline engine) installed in an automotive vehicle. The fuel injection control system adjusts the amount of fuel introduced into a combustion chamber based on a sensing result obtained by the air-fuel ratio sensing apparatus so as to realize the combustion with a target air-fuel ratio.

FIG. 1 is a circuit diagram showing a schematic arrangement of an air-fuel ratio detecting apparatus in accordance with the first embodiment of the present invention.

An air-fuel ratio detecting apparatus 15 comprises a microcomputer 20. The microcomputer 20 is connected to an engine control unit (i.e., ECU) 16 to perform interactive data communication for a fuel injection control, an ignition control or the like.

A limiting current type air-fuel ratio sensor (A/F sensor) 30 is installed in an exhaust pipe 12 extending from an engine body 11 of an engine 10. The A/F sensor 30 is responsive to a command voltage supplied from the microcomputer 20 and generates an air-fuel ratio sensing signal (i.e., sensor current signal) which is linear and proportional to the oxygen concentration in the exhaust gas.

The microcomputer 20, consisting of well-known components such as CPU, ROM, RAM for performing various computational processing, controls a bias controller 24 and a heater controller 26 according to a predetermined control program. The microcomputer 20 is connected to a battery +B to receive electric power for operation.

Figure 2:
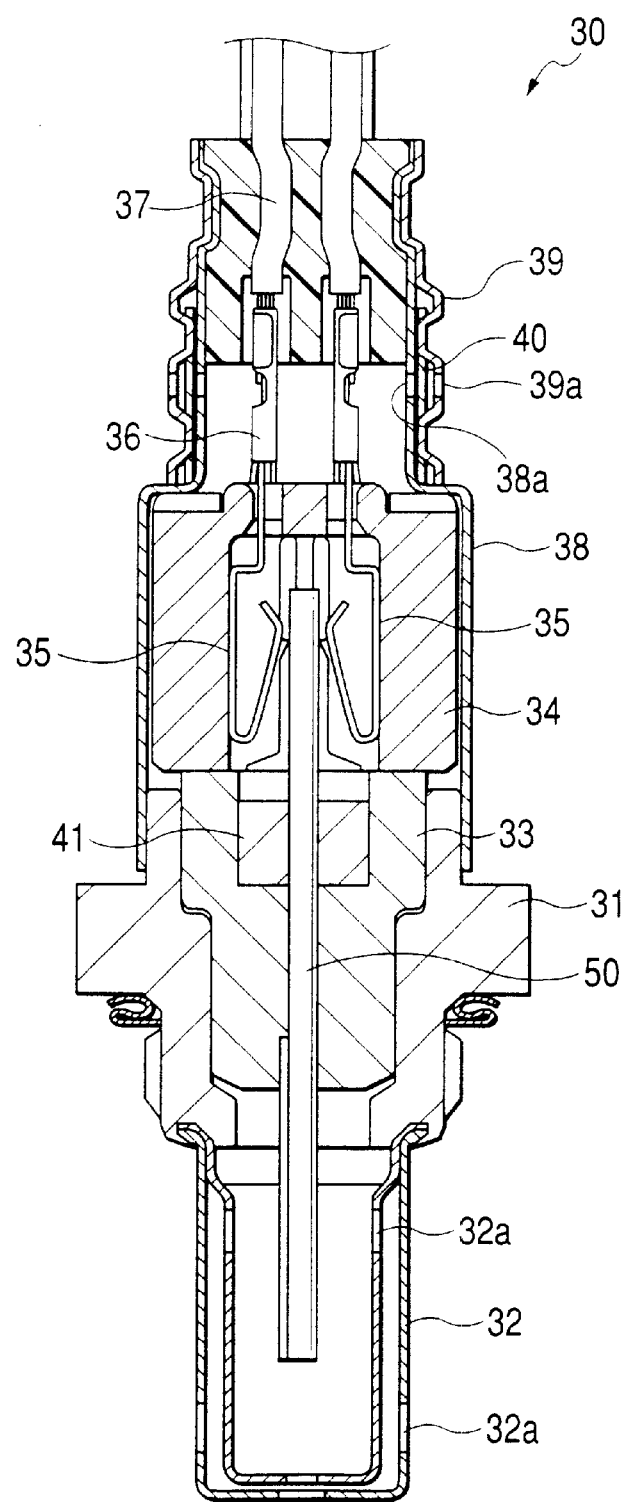
FIG. 2 is a vertical cross-sectional view showing an overall arrangement of an air-fuel ratio sensor in accordance with the first embodiment of the present invention.

FIG. 2 is a vertical cross-sectional view showing an overall arrangement of A/F sensor 30. As shown in FIG. 2, A/F sensor 30 comprises a metallic cylindrical housing 31 with a threaded outer portion securely fixed to a wall of exhaust pipe 12. The lower part of the housing 31 protrudes from the wall of exhaust pipe 12 and is exposed to the exhaust gas flowing in the exhaust pie 12. A double element cover 32, consisting of inner and outer cup-shaped covers, is attached to a lower opening end of the housing 31. A multilayered sensing element 50, configured into an elongated plate shape, extends in the axial direction of housing 31 so that the lower end of the sensing element 50 is placed in the inside space of the element cover 32. The element cover 32 is provided with a plurality of holes 32a which introduce the exhaust gas into the inside space of the element cover 32 for forming an exhaust gas atmosphere surrounding the lower end of the sensing element 50.

An insulating member 33, intervening between the sensing element 50 and the inside wall of the housing 31, supports the sensing element 50. A glass sealing member 41, located inside a bore formed at an upper portion of the insulating member 33, airtightly seals the clearance between the sensing element 50 and the insulating member 33. Another insulating member 34, provided on the insulating member 33, has an inside space in which the sensing element 50 is connected to four leads 35. Two of leads 35 are connected to electrodes of the sensing element 50 to output a sensing signal, while the remaining two leads 35 are used for supplying electric power to a heater of the sensing element 50. These leads 35 are connected to external signal lines 37 via connectors 36.

A body cover 38 is welded to the upper end of the housing 31. A dust cover 39 is attached to the upper end of body cover 38. These covers 37 and 38 cooperatively protect the upper portion of the sensor. A water repellent filter 40 is interposed between these covers 37 and 38 at an overlapped portion thereof. The covers 37 and 38 are provided with a plurality of holes 38a and 39a which introduce the air into the inside space of the covers 37 and 38.

As shown in FIGS. 3A and 3B, the sensing element 50 comprises a solid electrolytic substrate 51 which is configured into a platelike shape and a partially-stabilized zirconia member having oxygen ion conductivity. An exhaust gas side electrode 52 is provided on one surface of the solid electrolytic substrate 51. A reference gas side electrode 53 is provided on an opposite surface of the solid electrolytic substrate 51 so as to exposed to a reference gas stored in a reference gas chamber 65. These electrodes 52 and 53 are located at a distal end (i.e., lower end) of the sensing element 50. The exhaust gas side electrode 52 is integrally formed with a lead 54 provided on the surface of solid electrolytic substrate 51. The reference gas side electrode 53 is integrally formed with a lead 55 provided on the opposite surface of solid electrolytic substrate 51. The leads 54 and 55 extends from the corresponding electrodes provided at the distal end (i.e., lower end) to a proximal end (i.e., upper end) of the solid electrolytic substrate 51. The other ends of leads 54 and 55 are connected to terminals 56 and 57 provided at the proximal end of the solid electrolytic substrate 51. The terminals 56 and 57 are located parallel to each other on the same surface of the solid electrolytic substrate 51. The lead 54 and the terminal 56 and integrally formed on one surface of the solid electrolytic substrate 51. The lead 55 and the terminal 57 and connected across the solid electrolytic substrate 51. A coating portion 59, provided at the distal end (i.e., the lower end) of the sensing element 50, coats or covers the entire surface of exhaust gas side electrode 52.

Figure 5A:
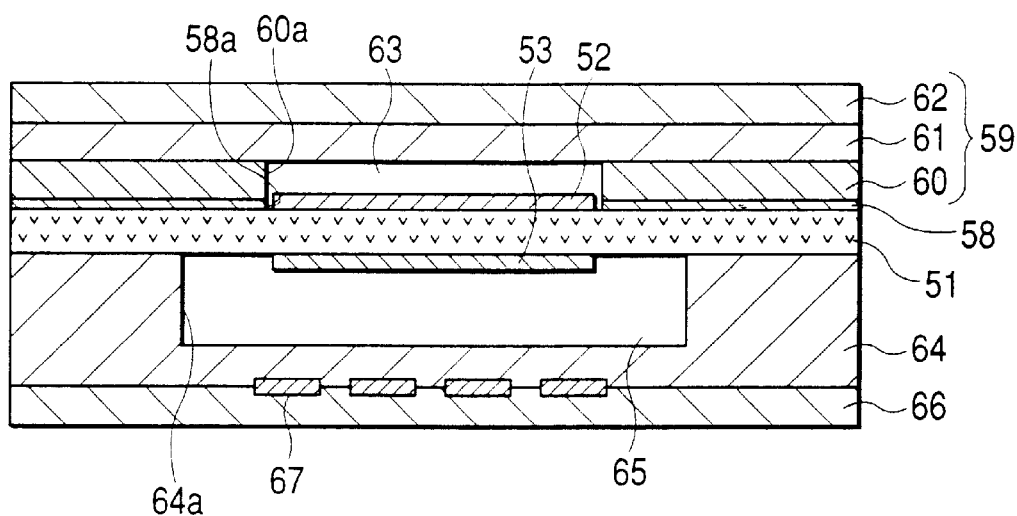
FIG. 5A is a cross-sectional view showing an essential arrangement of the sensing element in accordance with the first embodiment of the present invention.
Figure 5B:
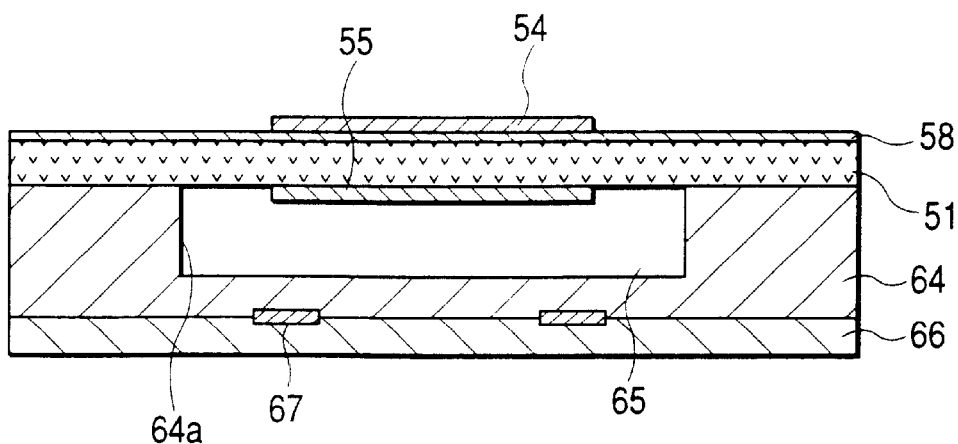
FIG. 5B is a cross-sectional view showing an essential arrangement of the sensing element in accordance with the first embodiment of the present invention.

As shown in FIGS. 4 and 5B, an insulating layer 58 is an gas-impermeable alumina member interposed between the solid electrolytic substrate 51 and the lead 54. FIG. 4 shows an appearance of the exhaust gas side electrode 52 which is directly formed on the solid electrolytic substrate 51 and not covered by the insulating layer 58. In other words, the insulating layer 58 has a window 58a through which the distal end (serving as the exhaust gas side electrode 52) of an electric conductor is directly connected to the surface of the solid electrolytic substrate 51. The remaining portion (serving as the lead 54) of the electric conductor is isolated from the solid electrolytic substrate 51 by the insulating layer 58. In FIG. 3A, a portion indicated by L1 is the lead 54. In FIG. 4, a portion indicated by hatching is the exhaust gas side electrode 52.

Figure 6:
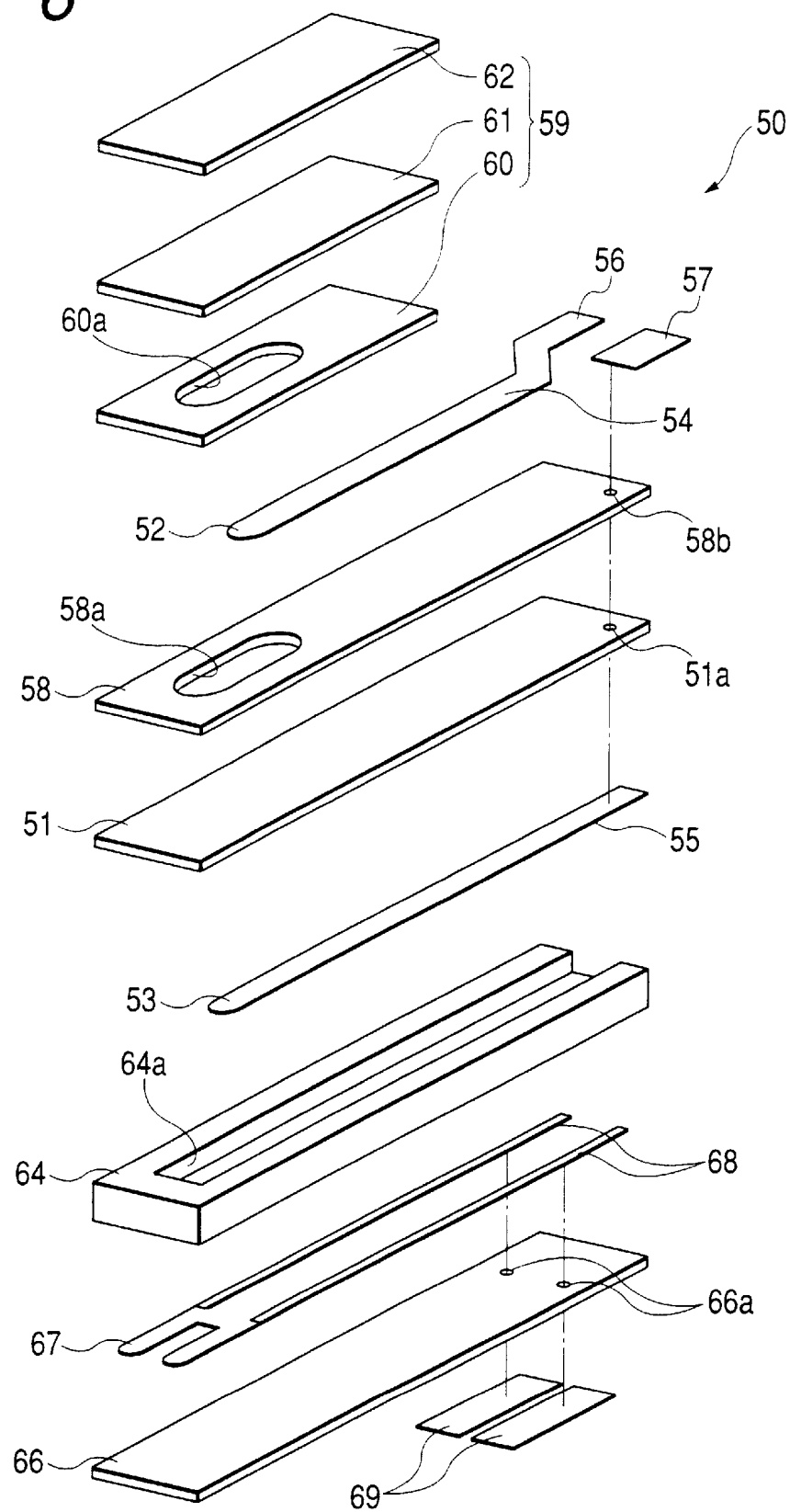
FIG. 6 is an exploded perspective view showing a detailed arrangement of the sensing element in accordance with the first embodiment of the present invention.

The exhaust gas side electrode 52, being a platinum member, is integrally formed with the lead 54 and the terminal 56 located on the surface of insulating layer 58 as understood from FIGS. 5A, 5B and 6.

The coating portion 59 has a multilayered structure consisting of a spacer 60 being a gas-permeable alumina ceramic member, a porous diffusion resistive layer 61 being an alumina ceramic member having a porosity of approximately 10%, and a gas shielding layer 62 being an alumina ceramic member having gas-shielding properties.

The spacer 60 has a window 60a at a predetermined position so as to just fit to the window 58a of insulating layer 58. The windows 58a and 60a cooperatively form a closed space 63 between the solid electrolytic substrate 51 and the porous diffusion resistive layer 61.

The reference gas side electrode 53, being a platinum member, is integrally formed with the lead 55 on the opposite surface of the solid electrolytic substrate 51. The proximal end of lead 55 is connected to the terminal 57 via an electric conductor of through-holes 51a and 58b extending across the solid electrolytic substrate 51 and the insulating layer 58.

A spacer 64, being an alumina ceramic member having electric insulating and gas-permeable properties, is laminated or stacked on the bottom (i.e., inner) surface of the solid electrolytic substrate 51. The spacer 64 has a groove 64a serving as the reference gas chamber 65. A heater substrate 66 is laminated or stacked on the bottom surface of the spacer 64. A heater 67 generates heat in response to electric power supplied via the lead 68. The heater 67 and the lead are provided on the same (i.e., inner) surface of the heater substrate 66. A pair of terminal 69, provided on an opposite surface of heater substrate 66, is connected to the leads 68 via electric conductors of through-holes 66a extending across the heater substrate 66.

Returning to FIG. 1, the microcomputer 20 produces a bias command signal Vr for applying a voltage to A/F sensor 30 (i.e., to sensing element 50). A digital-to-analog (D/A) converter 21 receives the bias command signal Vr produced as a digital signal from the microcomputer 20, and converts it into an analog signal Vb. A low-pass filter (LPF) 22 receives the analog signal Vb produced from D/A converter 21, and removing high-frequency components from the analog signal Vb to produce an LPF output Vc sent to the bias controller 24. The bias controller 24 produces a voltage corresponding to the present A/F with reference to predetermined application voltage characteristics, and applies the produced voltage to A/F sensor 30 during an A/F detecting operation. Furthermore, the bias controller 24 produces a voltage as a predetermined frequency signal applied to A/F sensor 30 in a one-shot manner with a predetermined time constant during an element impedance detecting operation.

The bias controller 24 includes a current detecting circuit 25 which detects a current value flowing across the A/F sensor 30 in response to the applied voltage. An analog-to-digital (A/D) converter 23 receives an analog signal representing the current value detected by the current detecting circuit 25, and converts it into a digital signal. The digital output signal of A/D converter 23 is sent to the microcomputer 20.

The heater controller 26 controls the operation of heater 67 provided in the sensing element 50. More specifically, the heater controller 26 performs a duty control of electric power supplied to the heater 67 based on the element impedance of A/F sensor 30.

The air-fuel ratio detecting apparatus 15 operates in the following manner.

Figure 7:
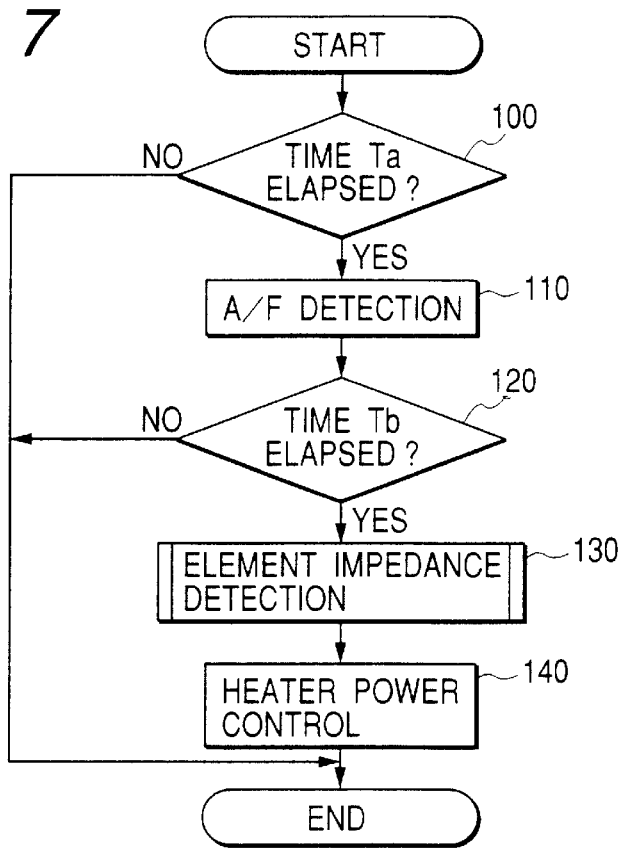
FIG. 7 is a flowchart showing a main routine of the control performed in a microcomputer in accordance with the first embodiment of the present invention.

FIG. 7 is a flowchart showing a main routine of the control performed in the microcomputer 20. The main routine is activated in response to the supply of electric power to the microcomputer 20.

In step 100, it is checked whether or not a predetermined time Ta has elapsed since the previous A/F detecting processing. The predetermined time Ta corresponds to a cycle (i.e., time period) of the A/F detecting processing. For example, a practical value of Ta is 4 msec.

When the time Ta has already elapsed (i.e., YES in step 100), the control flow proceeds to step 110 to execute the A/F detecting processing. In the A/F detecting processing, an application voltage is determined in accordance with the present sensor current and applied to the sensing element 50 of A/F sensor 30. The current detecting circuit 25 detects the sensor current flowing across the sensing element 50 in response to the applied voltage. The detected sensor current is converted into an A/F value.

Next, in step 120, it is checked whether or not a predetermined time Tb has elapsed since the previous element impedance detecting processing. The predetermined time Tb corresponds to a cycle (i.e., time period) of the element impedance detecting processing. For example, a practical value of Tb is variable for example from 128 msec to 2 sec in accordance with engine operating conditions.

When the time Tb has already elapsed (i.e., YES in step 120), the control flow proceeds to step 130 to execute the element impedance detecting processing. Details of the element impedance detecting processing will be explained later.

Then, the control flow proceeds to step 140 to execute the heater power control processing.

In step 140, a feedback control (e.g., PID control) is performed to equalize an actual value of element impedance ZAC to a target value (corresponding to an activated condition of the sensing element).

In other words, the processing of step 130 serves as a resistance detecting means of the present invention and the processing of step 140 serves as a heater control means.

Figure 8:
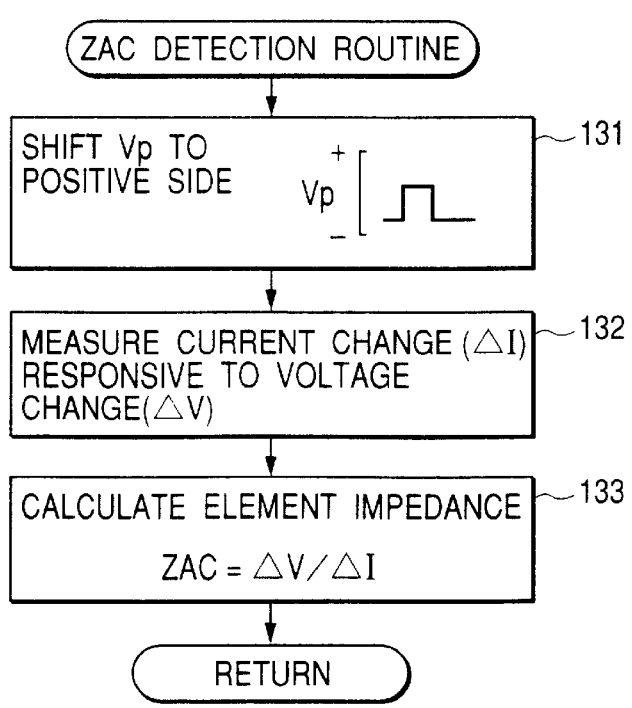
FIG. 8 is a flowchart showing a procedure for detecting an element impedance in accordance with the first embodiment of the present invention.

FIG. 8 is a flowchart showing the details of the element impedance (ZAC) detecting procedure performed in step 130.

According to this embodiment, the element impedance ZAC is detected as "alternating current impedance" based on a sweep method.

In step 131 of FIG. 8, the voltage applied for the A/F detection is changed to a positive side for a short period of several 10 to 100 µsec by adjusting the bias command signal Vr.

Then, in step 132, the current detecting circuit 25 measures a current change ($\Delta I$) responsive to a voltage change ($\Delta V$).

In the next step 133, the element impedance ZAC (=$\Delta V/\Delta I$) is calculated based on the measured current change ($\Delta I$) and the voltage change ($\Delta V$).

After completing step 133, the control flow returns to step 140 of FIG. 7.

Figure 9:
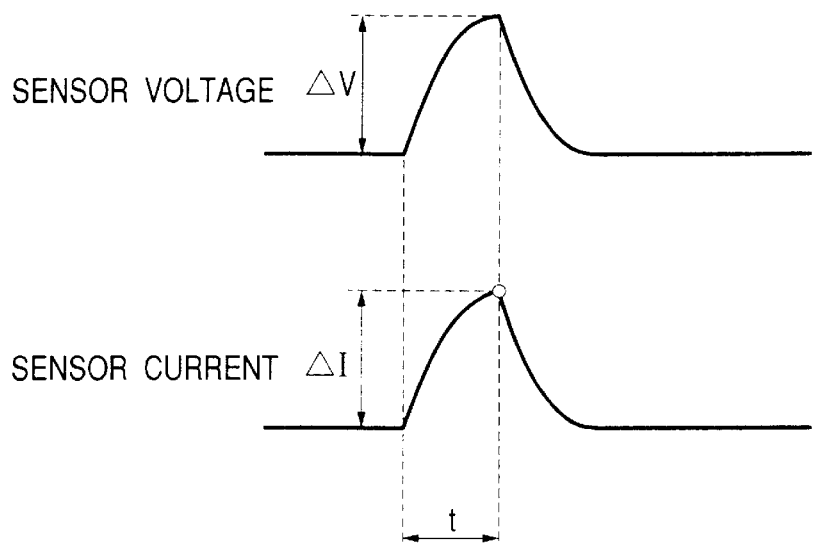
FIG. 9 is a graph showing a voltage change and a current change during the detection of an element impedance.

According to the above-described processing, a one-shot voltage having a predetermined time constant is applied to the A/F sensor 30 through LPF 22 and the bias control circuit 24 shown in FIG. 1. As a result, as shown in FIG. 9, the sensor current changes in response to the applied voltage and a peak current $\Delta I$ appears after a predetermined time 't'. The element impedance ZAC is obtained as a ratio of the voltage change ($\Delta V$) to the current change ($\Delta I$) measured in this transient period.

Interposing LPF 22 for applying the one-shot voltage to the A/F sensor 30 is effective to prevent the peak current from excessively increasing. This realizes reliable detection for the element impedance ZAC.

Figure 10:
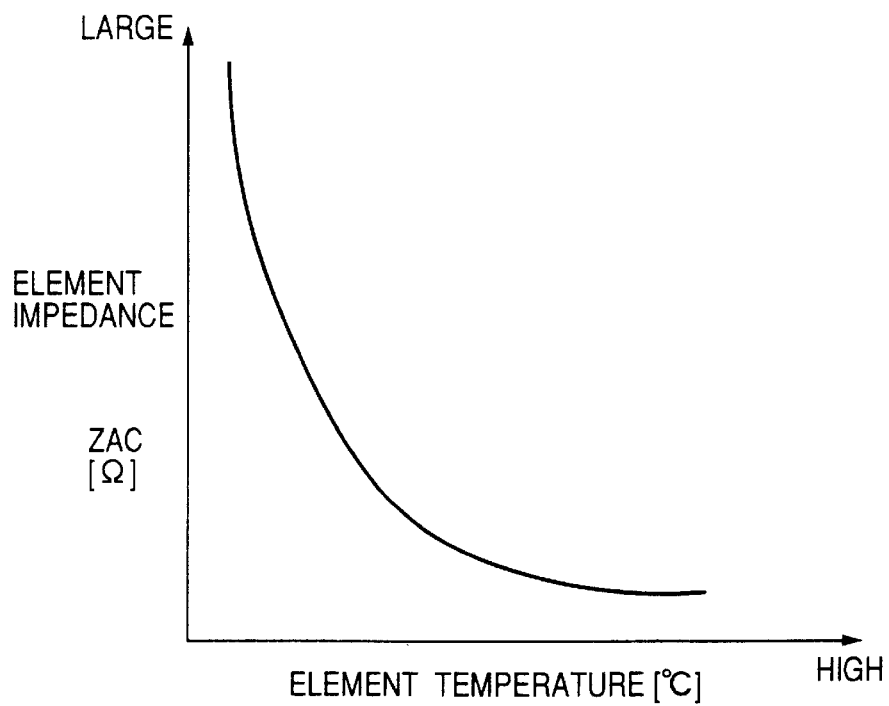
FIG. 10 is a graph showing a relationship between element impedance and element temperature.

As shown in FIG. 10, the element impedance ZAC greatly increases with reducing element temperature.

The sensing element 50 of A/F sensor 30 has the following temperature characteristics.

Figure 11:
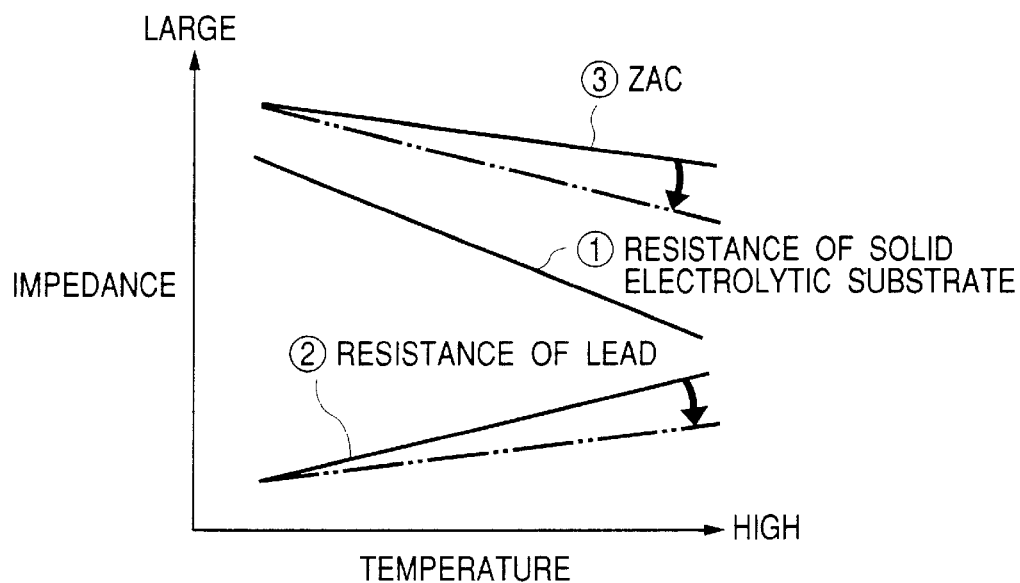
FIG. 11 is a graph showing a relationship between element impedance and temperature.

The solid electrolytic substrate 51 has negative temperature characteristics according to which the resistance value decreases with increasing temperature as indicated by a line ① in FIG. 11. On the contrary, each of the leads 54 and 55 has positive temperature characteristics according to which the resistance value increases with increasing temperature as indicated by a line ② in FIG. 11.

Thus, the measured element impedance ZAC, indicated by a line ③ in FIG. 11, is a sum of the resistance component of solid electrolytic substrate 51 and the resistance component of leads 54 and 55.

The element impedance ZAC is inherently a resistance component of the solid electrolytic substrate 51. However, the actually detected element impedance of a sensor includes the resistance component of the leads 54 and 55 whose temperature characteristics is opposite to that of the solid electrolytic substrate 51. Especially, when the A/F sensor 30 is in an activated condition (i.e., in a higher temperature region), the percentage of the lead resistance becomes large. This leads to deterioration of sensitivity of the element impedance ZAC. Accordingly, in the heater power control, the temperature controllability of sensing element 50 will be worsened.

In view of the above, this embodiment aims to reduce the percentage of the lead resistance component in the element impedance ZAC. Accordingly, this embodiment improves the sensitivity of element impedance ZAC in the sensor activated condition.

To this end, this embodiment introduces a ratio expressed by 'RL/ZS' which is a ratio of a resistance value 'RL' of leads 54 and 55 at a room temperature (i.e., in a sensor deactivated condition) to a resistance value 'ZS' of the element impedance in the sensor activated condition. The resistance value ZS is a target value of element impedance ZAC.

Figure 12:
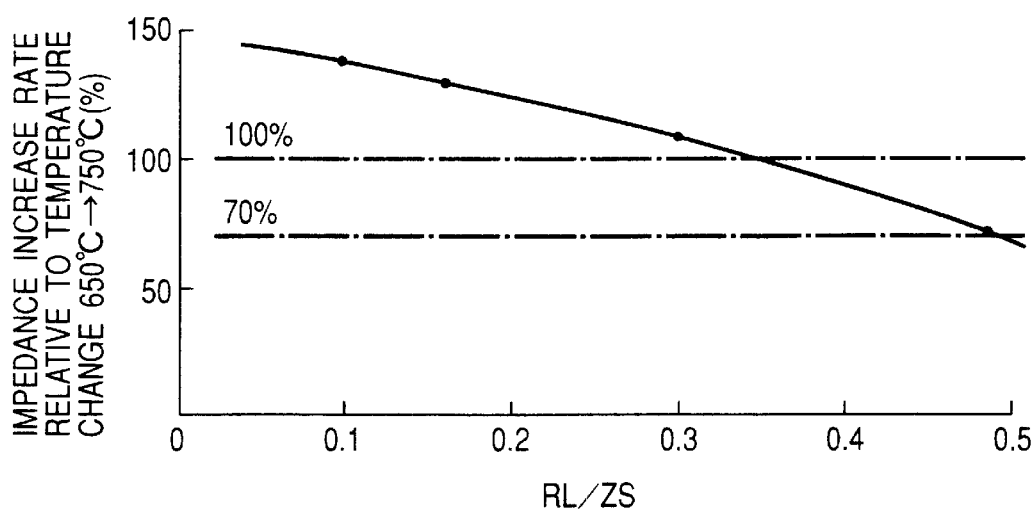
FIG. 12 is a graph showing a relationship between impedance increase rate and resistance ratio RL/ZS.

The inventors of this invention have observed an increase rate of element impedance ZAC responsive to the element temperature change from 650° C. to 750° C., to evaluate an adequate value of 'RL/ZS' for assuring the temperature controllability of sensing element 50. FIG. 12 shows the result.

In FIG. 12, the impedance increase rate is expressed according to the following equation.

Impedance Increase Rate (%)=(Z650/Z750−1)×100 where Z650 is an element impedance value at the element temperature 650° C. and Z750 is an element impedance value at the element temperature 750° C.

For example, when Z750 is equal to ½ of Z650, the impedance increase rate becomes 100 (%).

Regarding the evaluation level of impedance increase rate, a first evaluation level is set to 70% and a second evaluation level is set to 100%

As understood from the result shown in FIG. 12, the first evaluation level (i.e., impedance increase rate=70%) is attained when the ratio 'RL/ZS' is less than 0.5. The second evaluation level (i.e., impedance increase rate=100%) is attained when the ratio 'RL/ZS' is less than 0.3. In other words, the ratio 'RL/ZS' less than 0.5 assures adequate temperature controllability of sensing element 50. The ratio 'RL/ZS' less than 0.3 assures more adequate temperature controllability of sensing element 50.

In practice, restricting the percentage of lead resistance component is feasible by lowering the resistance value of the leads 54 and 55.

Figure 13A:
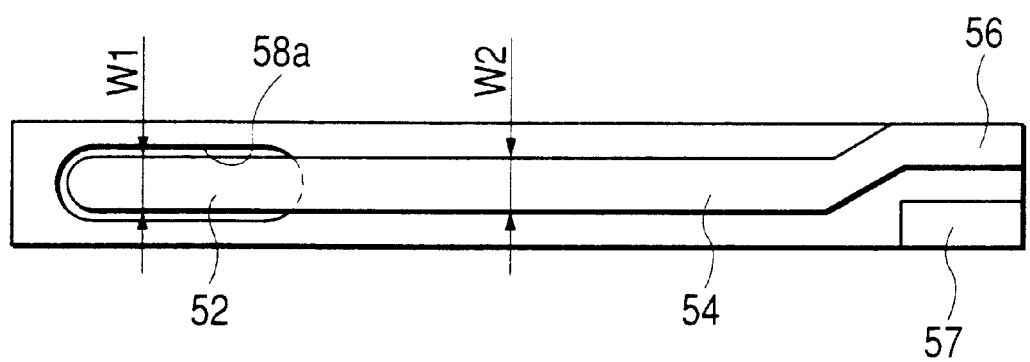
FIG. 13A is a plan view showing a characteristic arrangement of the sensing element in accordance with the first embodiment of the present invention.
Figure 13B:
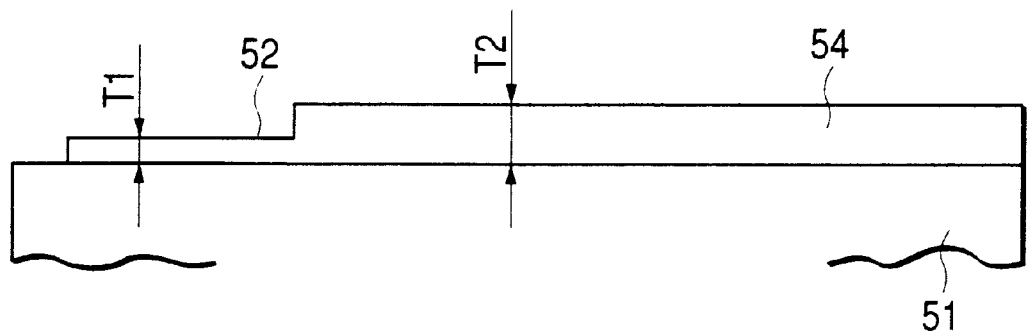
FIG. 13B is a side view showing a characteristic arrangement of the sensing element in accordance with the first embodiment of the present invention.

FIGS. 13A and 13B show the practical arrangement of sensing element 50 according to this embodiment, under the condition where the coating portion 59 is removed. The exhaust gas side electrode 52 and the lead 54 are partitioned by the window 58a of insulating layer 58. The exhaust gas side electrode 52 has a width W1 and a thickness T1. The lead 54 has a width W2 and a thickness T2.

According to the example shown in FIGS. 13A and 13B, the width W1 of exhaust gas side electrode 52 is equal to the width W2 of lead 54 (i.e., W1=W2). The thickness T2 lead 54 is two times the thickness T1 of exhaust gas side electrode 52 (i.e., T2=2×T1). In other words, a lateral cross section of lead 54 is two times a lateral cross section of exhaust gas side electrode 52 (i.e., W2·T2=2×W1·T1).

Employing the arrangement shown in FIGS. 13A and 13B makes it possible to effectively lower the resistance value of lead 54. In this case, the ratio 'RL/ZS' is approximately 0.1. The temperature characteristics of leads 54 and 55 can be changed from a solid line to an alternate long and two short dashes line shown in FIG. 11.

The practical arrangement of this embodiment is not limited to the example shown in FIGS. 13A and 13B. For example, it is preferable to arbitrarily increase the width W2 or the thickness T2 of the lead 54. For example, both of the width W2 and the thickness T2 of the lead 54 can be set larger than the width W1 and the thickness T1 of the exhaust gas side 52. According to the evaluation by the inventors, it is preferable that the lateral cross section (W2×T2) of the lead 54 is ½ to 5 times the lateral cross section (W1×T1) of the exhaust gas side electrode 52.

The above-described arrangement of exhaust gas side electrode 52 and lead 54 can be preferably employed for the reference gas side electrode 53 and its lead 55.

However, it is not always necessary to employ the same arrangement for each side of the sensing element 50. In this respect, this embodiment employs an arrangement for lowering the lead resistance at least one of the electric conductors provided on each side of the sensing element 50.

Important thing for this invention is to limit the ratio 'RL/ZS' to a predetermined range (for example, less than 0.3).

This embodiment brings the following effects.

According to the A/F sensor 30, the percentage of the resistance values of leads 54 and 55 with respect to the overall resistance value (i.e., element impedance ZAC) is restricted to a predetermined smaller range. This enhances the correlation between the resistance value of solid electrolytic substrate 51 and the element impedance ZAC. Thus, it becomes possible to adequately maintain or improve the sensitivity of element impedance ZAC in the sensor activated condition. The temperature characteristics of A/F sensor 30 can be improved. In other words, the element impedance ZAC explicitly reflects the resistance change of the solid electrolytic substrate 51.

Improving the temperature characteristics of A/F sensor 30 in the sensor activated condition leads to the improvement of the temperature control of the sensing element 50 performed by the air-fuel ratio detecting apparatus.

Second Embodiment

According to the A/F sensor 30, the heater 67 is provided in the vicinity of the electrodes 52 and 53. In general, the provision of a heater causes a temperature distribution in the gas sensing element. The temperature becomes high in the vicinity of the electrodes 52 and 53 compared with the signal output terminals 56 and 57.

Considering such temperature distribution, it is effective to reduce the resistance value of a limited lead portion closer to the electrodes 52 and 53.

To this end, the second embodiment modifies the configuration of the leads 54 and 55 in accordance with the temperature distribution in the sensing element 50.

Figure 14A:
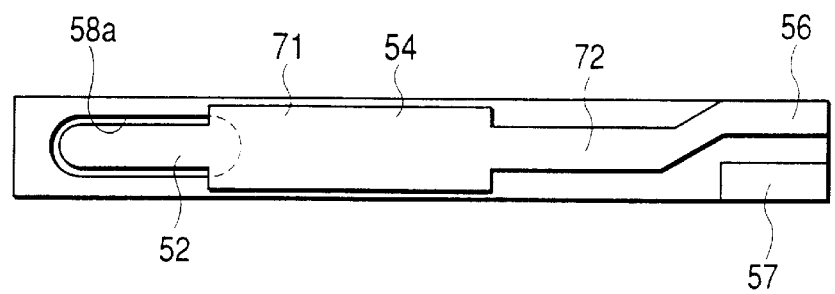
FIG. 14A is a plan view showing another characteristic arrangement of the sensing element in accordance with the first embodiment of the present invention.
Figure 14B:
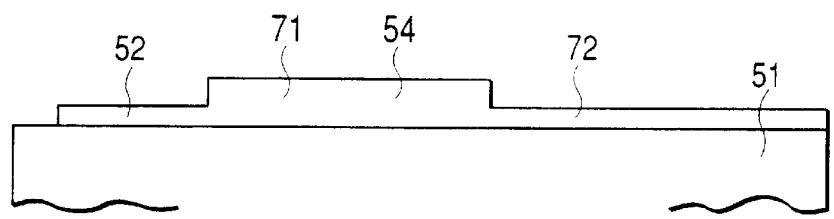
FIG. 14B is a side view showing another characteristic arrangement of the sensing element in accordance with the first embodiment of the present invention.

For example, as shown in FIGS. 14A and 14B, the lead 54 consists of a low resistance portion 71 located near the exhaust gas side electrode 52 and a high resistance portion 72 far from the exhaust gas side electrode 52. The low resistance portion 71 has a resistance value per unit length smaller than that of the high resistance portion 72. According to the example shown in FIGS. 14A and 14B, the lateral cross section of the lead 54 changes stepwise at the boundary between the low resistance portion 71 and the high resistance portion 72.

Figure 14C:
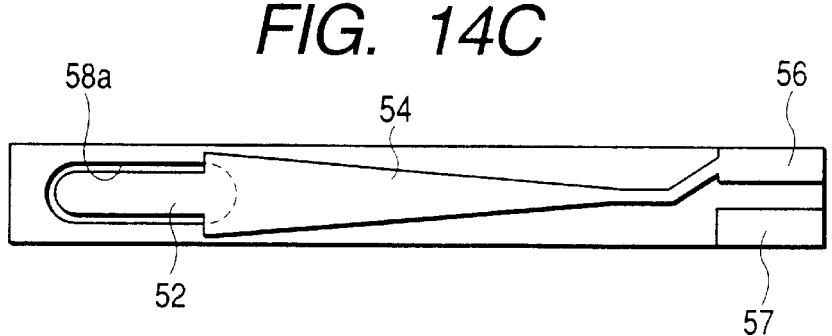
FIG. 14C is a plan view showing another characteristic arrangement of the sensing element in accordance with the first embodiment of the present invention.
Figure 14D:
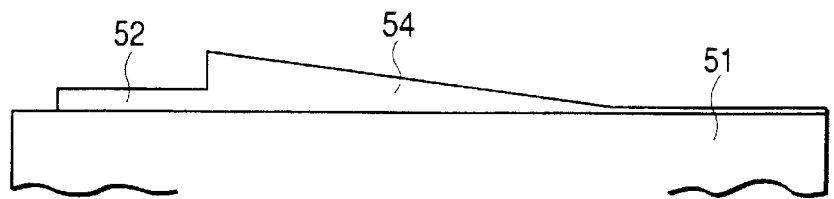
FIG. 14D is a side view showing another characteristic arrangement of the sensing element in accordance with the first embodiment of the present invention.

Alternatively, as shown in FIGS. 14C and 14D, the lead 54 has a lateral cross section which linearly decreases with increasing distance from the exhaust gas side electrode 52.

Needless to say, the arrangements shown in FIGS. 14A–14D can be applied to the lead 55.

According to the arrangement shown in FIGS. 14A–14D, the resistance values of leads 54 and 55 can be lowered at the limited region closer to the corresponding electrodes 52 and 53. In other words, the second embodiment effectively reduces the percentage of the resistance values of leads 54 and 55 with respect to the overall resistance value (i.e., element impedance ZAC) in the sensor activated condition. Thus, it becomes possible to improve the sensitivity of element impedance ZAC. The temperature characteristics of A/F sensor 30 can be improved. In other words, the element impedance ZAC explicitly reflects the resistance change of the solid electrolytic substrate 51.

Furthermore, according to the arrangement shown in FIGS. 14A–14D, a required amount of the material (usually a platinum or other noble metal) for leads 54 and 55 can be reduced. This makes it possible to reduce the cost of the leads 54 and 55.

According to the arrangement shown in FIGS. 14A–14D, the ratio 'RL/ZS' is restricted to be less than 0.5 or more preferably to be less than 0.3, like the first embodiment explained with reference to FIG. 12.

The present invention can be embodied in various ways. For example, lowering the resistance values of leads 54 and 55 is feasible by the following method or arrangement.

(1) When the leads 54 and 55 contain a ceramic material (e.g., $ZrO_2$) to improve the adhesion properties, it is preferable that an additive amount of the ceramic material is less than or equal to 12.5 wt %.

(2) The leads 54 and 55 are made of an electric conductive member having a resistance temperature coefficient less than or equal to $3 \times 10^{-3}/°$ C.

Figure 15:
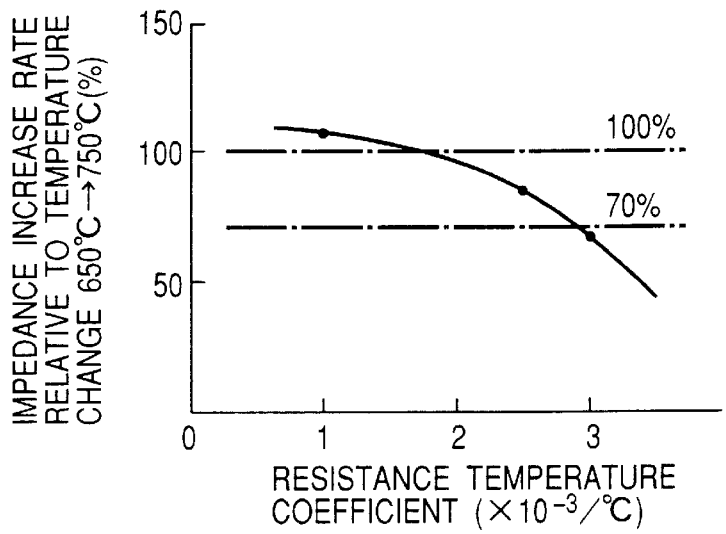
FIG. 15 is a graph showing a relationship between impedance increase rate and resistance temperature coefficient.

FIG. 15 shows a relationship between impedance increase rate and resistance temperature coefficient, wherein both the first evaluation level (i.e., impedance increase rate=70%) and the second evaluation level (i.e., impedance increase rate=100%) are set in the same manner as in FIG. 12.

As understood from FIG. 15, the first evaluation level is attained when the resistance temperature coefficient is less than or equal to $3 \times 10^{-3}/°$ C. In other words, the resistance temperature coefficient less than or equal to $3 \times 10^{-3}/°$ C. assures adequate temperature controllability of sensing element 50. The second evaluation level is attained when the resistance temperature coefficient is less than or equal to $2.5 \times 10^{-3}/°$ C. The resistance temperature coefficient less than or equal to $2.5 \times 10^{-3}/°$ C. assures more adequate temperature controllability of sensing element 50.

Figure 16:
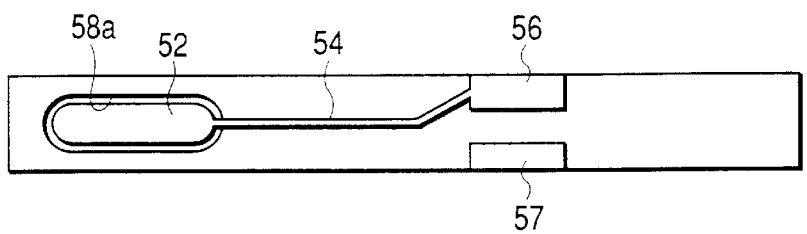
FIG. 16 is a plan view showing a characteristic arrangement of a sensing element in accordance with a second embodiment of the present invention.
Figure 17:
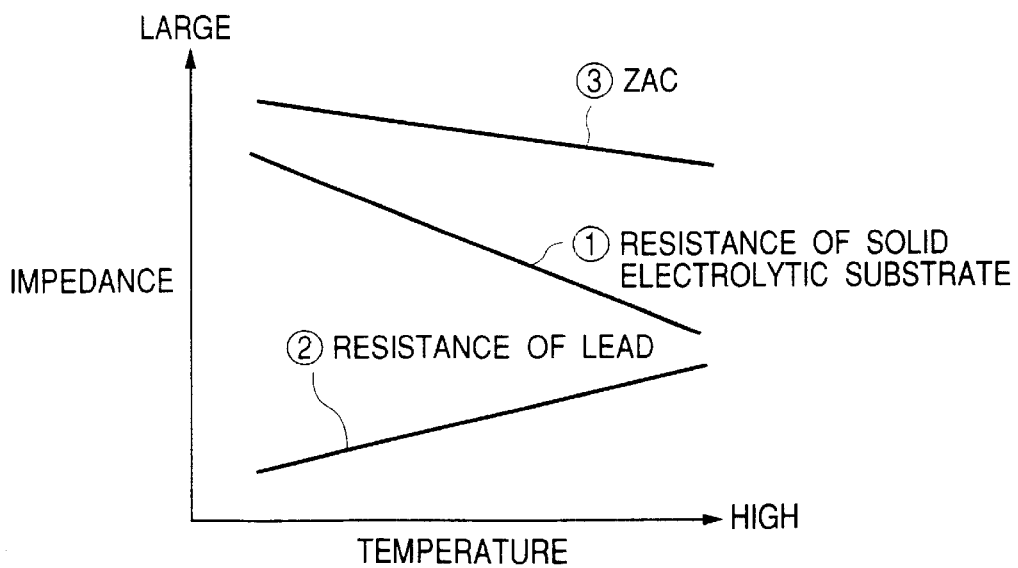
FIG. 17 is a graph showing a relationship between element impedance and temperature.

(3) The signal output terminals 56 and 57 are provided at intermediate portions of the solid electrolytic substrate 51 as shown in FIG. 16. This arrangement is advantageous to reduce the length of each lead 54 or 55 extending from the sensor electrode (i.e., the exhaust gas side electrode 52 or the reference gas side electrode 53) to its signal output terminal (56 or 57). As a result, the resistance values of leads 54 and 55 can be reduced.

Furthermore, the insulating layer 58 for isolating the lead 54 from the solid electrolytic substrate 51 is made of a material having a lower thermal conductivity. For example, the insulating layer 58 is a zirconia ($ZrO_2$) including no yttria ($Y_2O_3$). In this case, due to the provision of insulating layer 58 having a lower thermal conductivity, the lead 54 can be maintained at a relatively low temperature even if the exhaust gas side electrode 52 is heated up to a higher temperature. Accordingly, it becomes possible to improve the temperature characteristics of A/F sensor 30. Needless to say, the arrangements shown in FIG. 16 can be applied to the lead 55.

It is also preferable to differentiate the material for the leads 54 and 55 from the material for the exhaust gas side electrode 52 and the reference gas side electrode 53. For example, it is preferable to form the leads 54 and 55 by the material having a resistance value lower than that of a platinum (i.e., electrode material).

The present invention is applied to any A/F sensor detecting an oxygen concentration in the exhaust gas, but is also applicable to other type gas sensors, such as a NOx sensor detecting a NOx concentration in the exhaust gas, a CO sensor detecting a CO concentration in the exhaust gas, or the like. In such cases, the number of detecting cells (each cell consisting of a pair of electrodes) employed in a gas sensor is not limited to a specific value.

Furthermore, the present invention can be applied to any type of gas sensors detecting the concentration of a measured gas other than the exhaust gas of an engine. In this respect, the gas concentration detecting apparatus according to the present invention is not limited to an air-fuel ratio detecting apparatus.

What is claimed is:

1. A multilayered gas sensor comprising:
a solid electrolytic substrate having oxygen ion conductivity;
a measured gas side electrode provided on one surface of said solid electrolytic substrate;
a reference gas side electrode provided on an opposite surface of said solid electrolytic substrate so as to be exposed to a reference gas stored in a reference gas chamber;
a first lead having one end connected to said measured gas side electrode and the other end connected to a first signal output terminal; and
a second lead having one end connected to said reference gas side electrode and the other end connected to a second signal output terminal,
wherein the following relationship is satisfied $$B/A < 0.5$$

wherein 'A' represents an overall resistance value of an electric path including said solid electrolytic substrate, said electrodes, and said first and second leads in a sensor activated condition, while 'B' represents a resistance value of said first and second leads at a room temperature.

2. The multilayered gas sensor in accordance with claim 1, wherein said overall resistance value 'A' is a target resistance value for a sensor activation control.

3. The multilayered gas sensor in accordance with claim 1, wherein at least one of said first and second leads has a lateral cross section equivalent to ½ to 5 times a lateral cross section of a corresponding electrode.

4. The multilayered gas sensor in accordance with claim 3, wherein said at least one of said first and second leads is thicker than said corresponding electrode.

5. The multilayered gas sensor in accordance with claim 3, wherein said at least one of said first and second leads is wider than said corresponding electrode.

6. The multilayered gas sensor in accordance with claim 1, wherein said first and second signal output terminals are provided at intermediate portions of said solid electrolytic substrate.

7. The multilayered gas sensor in accordance with claim 1, wherein said first and second leads contain a ceramic material and an additive amount of said ceramic material in at least one of said first and second leads is less than or equal to 12.5 wt %.

8. The multilayered gas sensor in accordance with claim 1, wherein at least one of said first and second leads is made of an electric conductive member having a resistance temperature coefficient less than or equal to $3 \times 10^{-3}/°C$.

9. The multilayered gas sensor in accordance with claim 1, wherein said electrodes are bonded on the surfaces of said solid electrolytic substrate and an insulating layer having a low thermal conductivity is provided to isolate said first and second leads from said solid electrolytic substrate.

10. A gas concentration detecting apparatus using a multilayered gas sensor,
said multilayered gas sensor comprising:
a solid electrolytic substrate having oxygen ion conductivity;
a measured gas side electrode provided on one surface of said solid electrolytic substrate;
a reference gas side electrode provided on an opposite surface of said solid electrolytic substrate so as to be exposed to a reference gas stored in a reference gas chamber;
a first lead having one end connected to said measured gas side electrode and the other end connected to a first signal output terminal; and
a second lead having one end connected to said reference gas side electrode and the other end connected to a second signal output terminal,
wherein the following relationship is satisfied $$B/A < 0.5$$

wherein 'A' represents an overall resistance value of an electric path including said solid electrolytic substrate, said electrodes, and said first and second leads in a sensor activated condition, while 'B' represents a resistance value of said first and second leads at a room temperature, and
said gas concentration detecting apparatus comprising:
resistance detecting means for detecting a resistance value of said solid electrolytic substrate based on electric signals obtained from said signal output terminals, and
heater control means for controlling electric power supplied to a heater heating said solid electrolytic substrate based on the resistance value detected by said resistance detecting means.

11. A multilayered gas sensor comprising:
a solid electrolytic substrate having oxygen ion conductivity;
a measured gas side electrode provided on one surface of said solid electrolytic substrate;
a reference gas side electrode provided on an opposite surface of said solid electrolytic substrate so as to be exposed to a reference gas stored in a reference gas chamber;
a first lead having one end connected to said measured gas side electrode and the other end connected to a first signal output terminal;
a second lead having one end connected to said reference gas side electrode and the other end connected to a second signal output terminal; and
a heater for heating said electrodes,
wherein at least one of said first and second leads has a low resistance portion located in the vicinity of said electrodes and a high resistance portion located in the vicinity of said signal output terminals.

12. The multilayered gas sensor in accordance with claim 11, wherein a lateral cross section of said high resistance portion is smaller than that of said low resistance portion.

13. The multilayered gas sensor in accordance with claim 11, wherein the following relationship is satisfied $$B/A < 0.5$$

wherein 'A' represents an overall resistance value of an electric path including said solid electrolytic substrate, said electrodes, and said first and second leads in a sensor activated condition, while 'B' represents a resistance value of said first and second leads at a room temperature.

14. A gas concentration detecting apparatus using a multilayered gas sensor,
said multilayered gas sensor comprising:
a solid electrolytic substrate having oxygen ion conductivity;

a measured gas side electrode provided on one surface of said solid electrolytic substrate;

a reference gas side electrode provided on an opposite surface of said solid electrolytic substrate so as to be exposed to a reference gas stored in a reference gas chamber;

a first lead having one end connected to said measured gas side electrode and the other end connected to a first signal output terminal;

a second lead having one end connected to said reference gas side electrode and the other end connected to a second signal output terminal; and a heater for heating said electrodes, wherein at least one of said first and second leads has a low resistance portion located in the vicinity of said electrodes and a high resistance portion located in the vicinity of said signal output terminals, and said gas concentration detecting apparatus comprising:

resistance detecting means for detecting a resistance value of said solid electrolytic substrate based on electric signals obtained from said signal output terminals, and heater control means for controlling electric power supplied to a heater heating said solid electrolytic substrate based on the resistance value detected by said resistance detecting means.

15. A multilayered gas sensor comprising:

a solid electrolytic substrate having oxygen ion conductivity;

a measured gas side electrode provided on one surface of said solid electrolytic substrate;

a reference gas side electrode provided on an opposite surface of said solid electrolytic substrate so as to be exposed to a reference gas stored in a reference gas chamber;

a first lead having one end connected to said measured gas side electrode and the other end connected to a first signal output terminal;

a second lead having one end connected to said reference gas side electrode and the other end connected to a second signal output terminal; and a heater for heating said electrodes, wherein at least one of said first and second leads is configured in such a manner that a resistance value per unit length is smaller at a portion near said electrodes and is larger at a portion far from said signal output terminal electrodes.

16. The multilayered gas sensor in accordance with claim 15, wherein the following relationship is satisfied $$B/A < 0.5$$

wherein 'A' represents an overall resistance value of an electric path including said solid electrolytic substrate, said electrodes, and said first and second leads in a sensor activated condition, while 'B' represents a resistance value of said first and second leads at a room temperature.

17. A gas concentration detecting apparatus using a multilayered gas sensor, said multilayered gas sensor comprising:

a solid electrolytic substrate having oxygen ion conductivity;

a measured gas side electrode provided on one surface of said solid electrolytic substrate;

a reference gas side electrode provided on an opposite surface of said solid electrolytic substrate so as to be exposed to a reference gas stored in a reference gas chamber;

a first lead having one end connected to said measured gas side electrode and the other end connected to a first signal output terminal;

a second lead having one end connected to said reference gas side electrode and the other end connected to a second signal output terminal; and a heater for heating said electrodes, wherein at least one of said first and second leads is configured in such a manner that a resistance value per unit length is smaller at a portion near said electrodes and is larger at a portion far from said electrodes, and said gas concentration detecting apparatus comprising:

resistance detecting means for detecting a resistance value of said solid electrolytic substrate based on electric signals obtained from said signal output terminals, and heater control means for controlling electric power supplied to a heater heating said solid electrolytic substrate based on the resistance value detected by said resistance detecting means.

* * * * *